(12) United States Patent
Wang et al.

(10) Patent No.: US 7,796,262 B1
(45) Date of Patent: Sep. 14, 2010

(54) INTEGRATED OPTICAL RESONATOR DEVICE FOR MEASURING CHEMICAL AND BIOLOGICAL ANALYTE CONCENTRATIONS

(75) Inventors: Shaopeng Wang, Stillwater, OK (US); Akhilesh Ramachandran, Stillwater, OK (US); Edward T Knobbe, Stillwater, OK (US); Frederick Gorr Johnson, Ellicott City, MD (US); Brent Everett Little, Glen Head, NY (US); David Wesley Goad, Stillwater, OK (US)

(73) Assignee: Nomadics, Inc., Stillwater, OK (US)

( * ) Notice: Subject to any disclaimer, the term of this patent is extended or adjusted under 35 U.S.C. 154(b) by 771 days.

(21) Appl. No.: 11/809,867

(22) Filed: May 31, 2007

(51) Int. Cl.
*G01N 21/00* (2006.01)
(52) U.S. Cl. .................................. 356/436; 356/441
(58) Field of Classification Search ......... 356/432–448, 356/450–458
See application file for complete search history.

(56) References Cited

U.S. PATENT DOCUMENTS

| | | | |
|---|---|---|---|
| 5,663,790 A | 9/1997 | Ekstrom et al. | |
| 6,490,039 B2 * | 12/2002 | Maleki et al. | 356/436 |
| 6,507,684 B2 | 1/2003 | Tapalian et al. | |
| 6,583,399 B1 | 6/2003 | Hunziker et al. | |
| 6,657,731 B2 | 12/2003 | Tapalian et al. | |
| 6,661,938 B2 | 12/2003 | Lim et al. | |
| 6,721,053 B1 | 4/2004 | Maseeh | |
| 6,781,696 B1 | 8/2004 | Rosenberger et al. | |
| 6,795,481 B2 | 9/2004 | Maleki et al. | |
| 6,876,796 B2 * | 4/2005 | Garito et al. | 385/50 |
| 6,885,794 B2 | 4/2005 | Scheuer et al. | |
| 7,248,771 B2 * | 7/2007 | Schmidt et al. | 385/129 |
| 7,384,797 B1 * | 6/2008 | Blair | 436/524 |
| 2004/0023396 A1 | 2/2004 | Boyd et al. | |
| 2006/0170931 A1 | 8/2006 | Guo et al. | |

FOREIGN PATENT DOCUMENTS

| | | |
|---|---|---|
| WO | WO 01/40757 A2 | 6/2001 |
| WO | WO 2005/019798 A2 | 3/2005 |

OTHER PUBLICATIONS

"Resonators and Q Value" by Johan Liljencrants, Web site at http://mmd.foxtail.com/Tech/qval.html, visited May 15, 2007.
"Guided-Wave Optical Biosensors" by Vittorio M. N. Passaro, Sensors, ISSN 1424-8220, 2007 by MDPI.
"Analysis of active antibody concentration. Separation of affinity and concentration parameter." by Robert Karlsson et al, Johnson of Immunological Methods, 166 (1993) 75-84.

* cited by examiner

*Primary Examiner*—Gregory J Toatley, Jr.
*Assistant Examiner*—Jarreas C Underwood
(74) *Attorney, Agent, or Firm*—McAfee & Taft

(57) ABSTRACT

The current invention provides methods for detecting trace analytes in solution or suspension using coupled micro-ring resonators. The methods of the current invention determine the presence and concentration of the target analytes in real time by exposing the micro-ring resonator to the analyte and determining the resulting rate of change of resonance wavelength experienced by a sensing micro-ring resonator as compared to a reference micro-ring resonator.

37 Claims, 4 Drawing Sheets

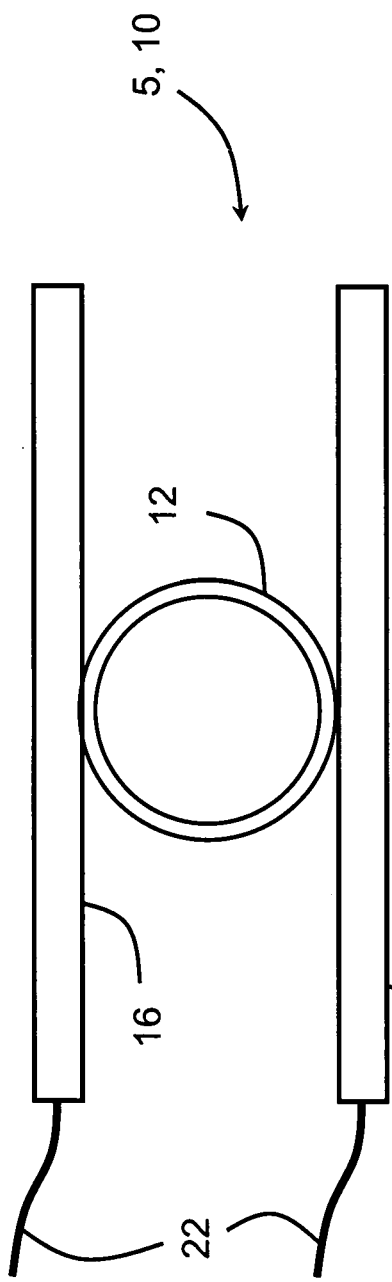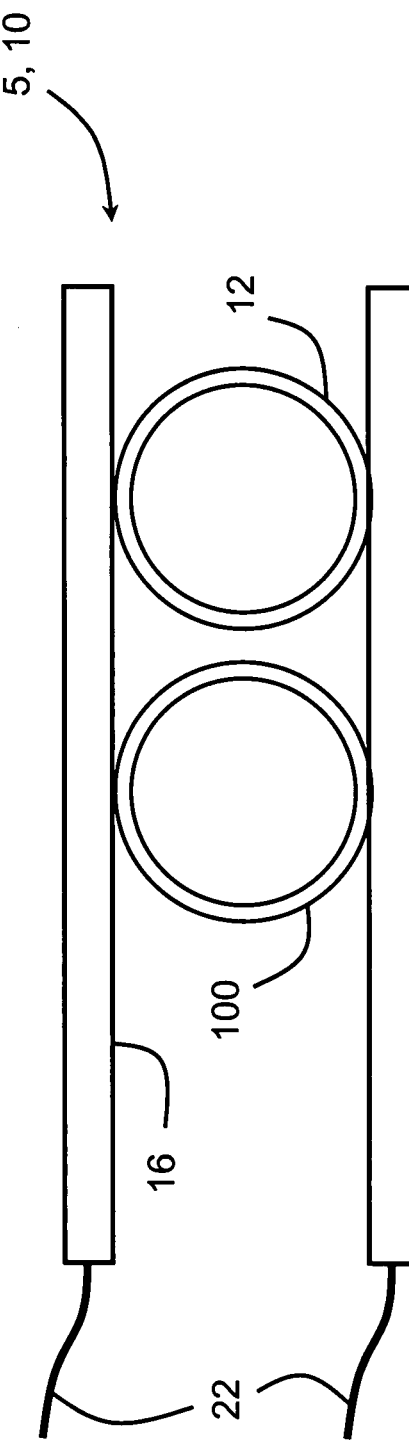

INTEGRATED OPTICAL RESONATOR DEVICE FOR MEASURING CHEMICAL AND BIOLOGICAL ANALYTE CONCENTRATIONS

STATEMENT AS TO FEDERALLY SPONSORED RESEARCH

This application was supported in part by a contract from DARPA Contract #W81XWH-04-C-0139 Subcontract 70030-NOM. The United States Government may have rights in and to this application by virtue of this funding.

BACKGROUND

A number of platforms have been developed for chemical and biological sensing including optical techniques such as infra-red absorption, surface plasmon resonance (SPR) sensors, florescence-based sensors, and several methods employing optical resonators. These optical resonator sensor designs are attractive solutions as they tend to have a small form factor and can be designed with high sensitivities. Optical resonator sensor platforms can be categorized into two groups: multimode whispering gallery devices and single mode waveguide resonator devices.

Whispering gallery mode (WGM) devices tend to focus on changes in optical absorption and the effect on the resonator quality factor. These devices have been used as sensors when incorporating a microsphere selected to measure optical absorption at a predetermined wavelength. Additionally, when coated with a film suitable for interacting with and binding analytes of interest, the resonator will experience a change in the Q-factor as analyte is bound to the resonator. The Q-factor is altered through increased loss such that a change in the intensity of the optical transmission spectrum coupled through the resonator can be observed. Other WGM sensors rely on an interaction between the resonator surface and a molecular species of interest to change the effective refractive index of the set of optical modes supported by the WGM resonator. The resulting change in phase and/or resonant wavelength of these optical modes can be measured.

Whispering gallery mode resonators, such as microspheres typically have Q values of $10^9$ and higher. Although high Q values are advantageous, WGM resonators tend to support a dense optical spectrum of modes which increases the difficulty in tracking the resonant wavelength of one specific mode. As a result, WGM sensor designs tend to rely on sensing changes in optical intensity related to changes in the cavity Q. Thus, WGM resonators are more susceptible to signal to noise issues relating to small variations in optical intensity due to environmental factors and coupling variations as well as source and detector related intensity noise.

An additional drawback related to the large number of optical modes is that WGM must generally rely on self-referencing. This method of referencing relies on comparing two measurements taken at different times, one measurement before the interaction occurs and a second measurement after the endpoint of the interaction. For example, sensor measurements are usually measured by referencing a change in intensity resulting from interaction of the WGM resonator with a specific analyte to a prior baseline intensity measurement taken just before exposure of the resonator to the analyte. These measurements can experience error due to environmental effects occurring after the first measurement or by secondary interactions such as non-specific binding.

Optical resonators based on single mode waveguides generally have lower Q values than WGM resonators. However, they offer the advantage of supporting only a single transverse spatial optical mode. For example, a micro-ring resonator fabricated from a rectangular cross-section waveguide can be designed to support only the lowest order transverse spatial mode, which generally consists of one transverse electric (TE) polarized mode as well as a second transverse magnetic (TM) polarized mode. The resulting transfer function consists of a single set of TE and TM temporal modes at resonant wavelengths given by $$\lambda_i = 2\pi r n / i$$

where r is the ring radius, n is the optical waveguide effective index, and i is an integer.

Thus, a single mode resonator design for a sensor permits transmission of an optical signal through a waveguide such that is passes by and interacts with a resonator. Some of the light couples from waveguide to resonator such that the waveguide's transmission spectrum contains a dip in intensity corresponding to the resonator resonance. The shift in the dip of the transmission spectrum corresponds to a change in resonance resulting from specific binding of a material to the resonator surface. The shift is measured and compared to the shift seen in a second reference ring. Alternatively the relative difference in the resonance shifts observed for TE and TM polarized optical signals that are coupled to an optical resonator may be measured. In general, current single mode resonator devices focus on monitoring the position of the dip in the transmission spectrum of light traveling the through a waveguide.

The single mode resonator configuration shown in FIG. 1a is known as an all-pass filter design or a through configuration. In this example, whenever the wavelength of the input signal matches one of the resonances of the ring resonator light couples from the waveguide to the resonator. Light propagating within the resonator experiences some optical loss before coupling back to the through waveguide producing a dip in the transmission spectrum as shown in FIG. 1b.

In this design, the strength of the signal is related to the optical loss experienced by light traversing the ring resonator. An optical resonator with near zero loss will result in a very shallow dip in the transmission spectrum. This limits the sensitivity of the detection algorithm as intense noise fluctuation may hide the real signal. Compensating for this limitation requires intentionally increasing the loss in the ring. However, a higher loss results in a lower cavity Q and a broader resonance which in turn increases the difficulty in determining the precise resonant wavelength. Thus, one would prefer to have both a narrow resonance (high Q) as well as a high signal to noise ratio to best monitor the resonator resonance.

Current existing designs determine a net resonance shift, $\Delta\lambda$, at the endpoint by measuring the resonant wavelength of an active sensing ring after exposure to a material of interest and comparing the result to either the resonance of same ring before exposure or to that of a second reference ring. This method is ideal for determining the refractive index of a sample exposed to the ring resonator sensor and does well in sensing the absence or presence of a specific material of interest. However, this arrangement is not well suited for determining the precise level or concentration of material from the resonance shift after a fixed time. For example, the relative concentration of the material of interest must be known before exposure to the ring sensor to ensure the choice of an adequate endpoint time in order to both avoid overexposure and saturation effects as well as underexposure and non-observance of the shift in resonance.

There are a number of prior art references describing biological and chemical sensors based on optical resonators.

These optical resonator detection schemes may be categorized as using multimode whispering gallery resonators (i.e., microspheres, microdisks, . . . ) or single mode waveguide resonators (i.e., ring resonators). Techniques using devices rely on endpoint detection schemes where the shift in resonant wavelength is measured at the end of a fixed interval of time. As such, prior art methods do not provide for real time analysis.

SUMMARY OF THE INVENTION

The current invention overcomes the limitations of prior art by providing a method of measuring the binding rate of analytes to a micro-ring sensor by comparing the rate of change in the resonance of the sensor ring to that of a reference ring and relating this to the analyte concentration. In a preferred embodiment, the method of the current invention utilizes an array of vertically coupled micro-ring resonators wherein at least one micro-ring resonator is an active sensing resonator and at least one resonator is a reference or control resonator.

In one embodiment, the present invention provides a method wherein the net rate of change in the resonant peak, $d\lambda/dt$, for the sensor resonator is compared to the net rate of change to a control resonator to determine the concentration of the target analyte. In the method of the current invention the measured signal is the drop signal from the micro-ring resonator. In the current invention, the input optical signal travels along the add waveguide. Portions of the signal's spectrum couple to the micro-ring resonator when they match the resonance of the micro-ring. Subsequently, the output signal is collected by the drop waveguide and travels to a detector for processing. The signal transmitted to the detector at the output of the second waveguide corresponds to a peak or set of peaks at each resonant wavelength supported by the micro-ring resonator.

In one preferred embodiment, the current invention provides real time analysis by comparing measurements from an active resonator to a reference or control resonator. The active sensor resonator is a micro-ring resonator with a coating selected to specifically bind the analyte of interest to the resonator surface. Binding of the analyte to the surface of the micro-ring resonator changes the effective refractive index of the resonator. The control resonator is similar to the active resonator sensor but lacks the binding agent. Thus, although exposed to the analyte, the control resonator does not experience a change in resonant wavelength corresponding to binding of analyte to the control resonator outer surface. To determine the concentration of the analyte, the current invention measures the rate of change, $d\lambda/dt$, of the resonant peak position by comparing the active resonator to the control resonator. In a regime where the analyte concentration is low and specific binding to the resonator surface is limited by mass transport, the rate of change in the resonator resonant peak position is directly correlated to the analyte concentration. By measuring the rate of change of the resonant peak from the active analyte sensor ring in real time and comparing this to rate of change seen for a reference or control ring, the analyte concentration may be determined. By subtracting the two rates of change, a real time measurement of the rate of change in resonance is determined that is directly proportional to the analyte concentration.

In one preferred embodiment, the current invention provides a method for determining the concentration of an analyte in a suspension or a solution. The method utilizes a first coupled resonator comprising, a micro-ring resonator coupled to an input waveguide and an output waveguide. The output wave guide being optically coupled to a detector. Additionally, a second coupled resonator comprising, a micro-ring resonator coupled to an input waveguide and an output waveguide, said output wave guide being optically coupled to a detector is used a reference resonator. Preferably, both coupled resonator may be provided on a single chip as an array. The sensing microring resonator is prepared by applying receptors suitable for binding the analyte of interest to the micro-ring resonator of said first coupled resonator. After application of the receptors, the microring resonators are contacted with a solution or suspension containing the analyte of interest while passing light through said input waveguide(s). Subsequently, the presence and concentration of the analyte is determined by comparing the rate of change in resonance wavelength of the sensing micro-ring resonator in the first coupled resonator to the rate of change in resonance wavelength of the micro-ring resonator in the second coupled resonator.

In an alternative embodiment, the current invention provides another method for determining the concentration of an analyte. In this embodiment the method utilizes a coupled resonator comprising, a first micro-ring resonator (the sensing micro-ring) coupled to an input waveguide and coupled to an output waveguide, the output wave guide being optically coupled to a detector. Additionally, a second micro-ring resonator (reference micro-ring) is coupled to the same input waveguide and output waveguide as the first micro-ring resonator. The sensing micro-ring resonator is prepared by applying receptors suitable for binding the analyte of interest to the micro-ring resonator. Subsequently, light is directed through the input wave guide while the coupled resonator is contacted with a solution or suspension containing the analyte of interest. The light output from each micro-ring is combined onto the output waveguide and directed to a detector. The detector determines the relative difference in the rates of change of the resonant wavelengths experienced by each micro-ring resonator thereby determining the presence and concentration of said analyte of interest.

BRIEF DESCRIPTION OF THE DRAWINGS

FIG. 1b depicts the transmission spectrum due to the resonance of the micro-ring resonator depicted in FIG. 1a.

FIG. 2 depicts a micro-ring resonator coupled to an input waveguide and an output waveguide.

FIG. 4 depicts an alternate arrangement of two micro-ring resonators coupled to an input waveguide and an output wave guide suitable for use in the current invention.

DETAILED DESCRIPTION

Figure 1A:
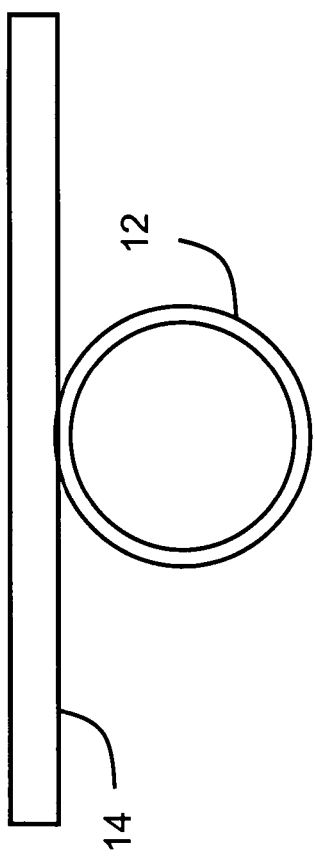
FIG. 1a depicts an all-pass micro-ring resonator and a coupled waveguide.
Figure 1B:
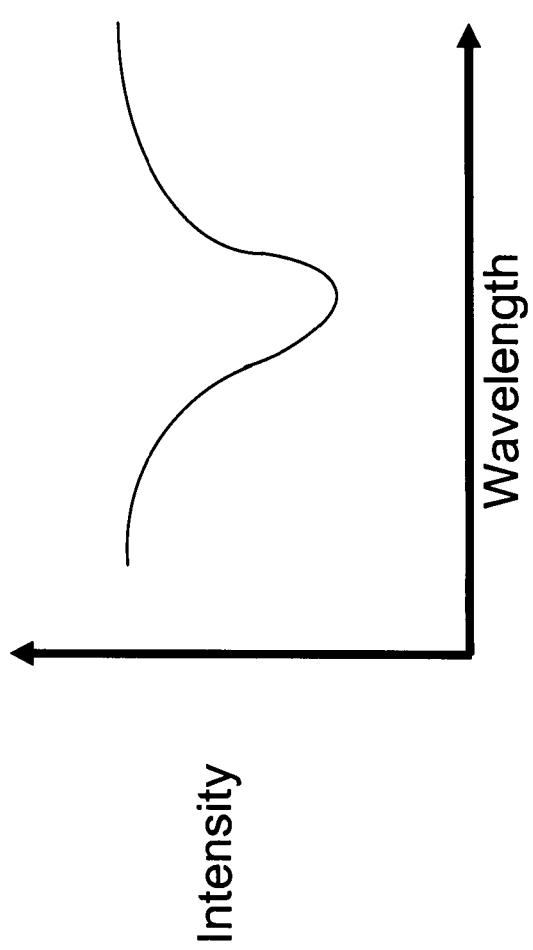

The current invention utilizes micro-ring resonators to provide real time analysis of trace analytes. A typical micro-ring usually has resolution power of about 7,000~14,000. The sensing dynamic range of a typical micro-ring resonator, as defined by the free spectrum range, is about 4 nm. As known to those skilled in the art, micro-ring resonators operate based on wave-guiding phenomena specified by boundary conditions. Propagation of light through narrow waveguides generates an evanescent field, a local region of light 'leakage', around the surface of the waveguide that extends a distance of 100-300 nm at near infrared wave length. The intensity of the evanescent field decays exponentially as the distance from the surface increases. When the waveguides and micro-rings are precisely aligned and positioned, either vertically or laterally, coupling of their evanescent fields can be achieved. This facilitates certain wavelengths (resonance wavelengths) of light passing through the input waveguide to enter into the micro-ring. Thus, to detect the attachment of analyte contained in the samples the micro-ring resonator uses an evanescent wave.

In a preferred embodiment, the methods of the current invention utilize an integrated optical resonator device 5 wherein the surface of the micro-rings 12 are coated with receptors (not shown) suitable for binding the analyte of interest. Preferably, device 5 is a micro-ring 12 coupled with at least two waveguides 14, 16 as depicted in FIG. 2. The combination of micro-ring 12 with waveguides 14, 16 is referred to herein as a coupled resonator 10 where waveguide 14 is the "add" or input waveguide and waveguide 16 is the drop or output waveguide.

With reference to FIG. 2, the size and effective refractive index (RI) of the micro-ring 12 structure determines the resonance characteristics. Effective coupling between micro-ring 12 and waveguide 14 is attained when the optical resonance condition in equation (1) is satisfied:

$$2\pi R \cdot \eta = \lambda \cdot m \quad (1)$$

where, R is the radius of the micro-ring, η represents the effective RI of the micro-ring, λ denotes the wavelength, and m is any integer. The product of ring circumference (2πR) and effective RI (η) is termed the optical path length (OPL). Once a particular wavelength of light that satisfies the conditions for optical resonance becomes coupled into the micro-ring, it is 'trapped' and continuously re-circulates, until a fraction of it eventually escapes by coupling into the output waveguide 16. This continuous recirculation of light within the structure of micro-ring resonator enhances the effective path length over the actual path length of the ring. As an increasing amount of light from the input waveguide becomes coupled into the micro-ring, the intensity of light within the ring structure builds up significantly, generating an amplified evanescent field for sensing applications.

In the current invention, micro-ring resonators 12 are used as label-free platforms for qualitative and quantitative biosensing using different types of biomolecules as receptors carried by micro-ring resonators 12. Each micro-ring resonator 12 has at least one optical resonance and the temporal rates of change of the optical resonance wavelength (or frequency) of the micro-ring resonator 12 is a function of the relative concentration of at least one analyte of interest. Biosensing was achieved by functionalizing micro-ring surfaces with receptors such as but not limited to antibodies or oligonucleotide probes. These molecules are nanoscaled and remain well within the evanescent sensing field of micro-rings 12. Specific binding of complementary target molecules to the surface-bound receptors induces an alteration in the effective RI within the evanescent field of micro-ring 12 which is detected based on resultant shift in resonance wavelength. The rate of the shift is used to calculate the concentration of the target molecules, i.e. the target analyte.

Figure 3:
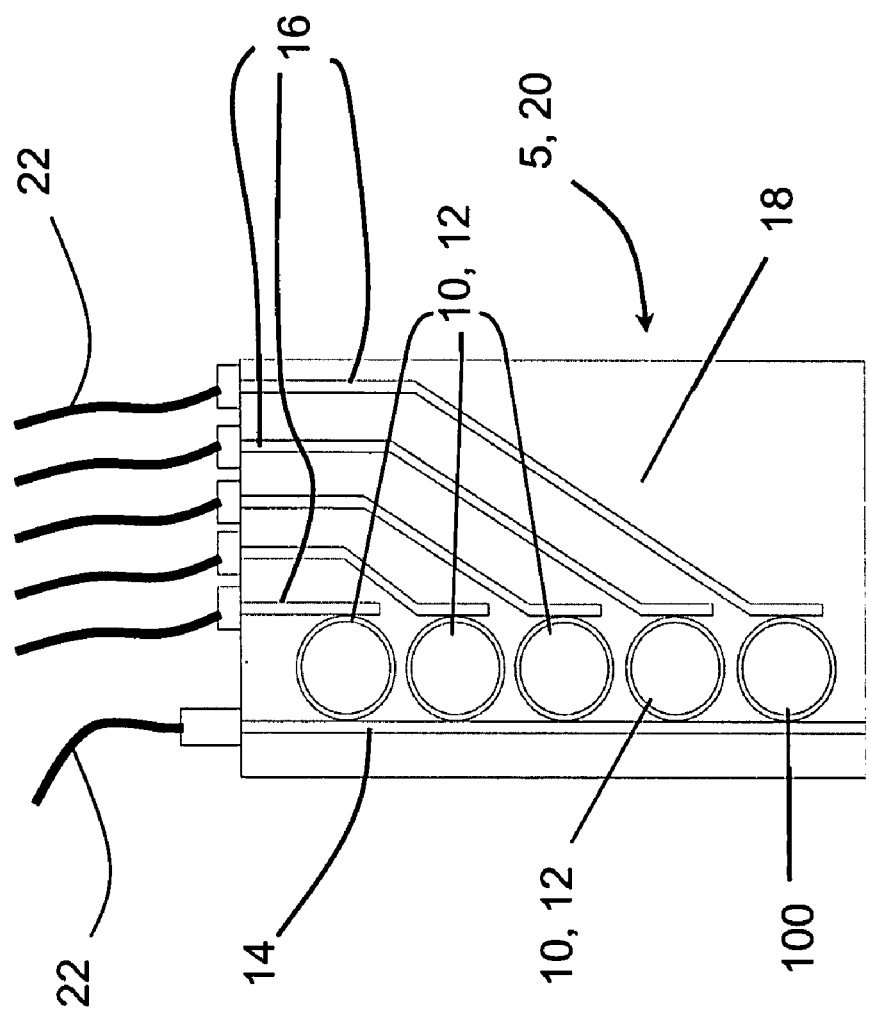
FIG. 3 depicts an array of coupled micro-ring resonators and waveguides on a single chip.

One skilled in the art is familiar with the methods of constructing an array 20 of coupled resonators 10 as depicted in FIG. 3. For the purposes of the following discussion, the coupled resonator 10 were fabricated on silicon chips 18 by optical photolithographic techniques using a low loss, high refractive index (RI) doped silica glass. Suitable material includes but is not limited to HYDEX high refractive material as described in U.S. Pat. Nos. 6,614,977, 6,771,868 and 6,768,828, each reference being incorporated herein by reference. As depicted in FIG. 3, each device 5 comprised five coupled resonators 10 (micro-rings 12 optically coupled to individual input 14 and output 16 waveguide buses) wherein one coupled resonator 10 is a reference resonator 100. The input and output waveguides 14, 16 were fabricated such that they were buried beneath the chip surface and vertically coupled to the micro-ring resonator 12 structure. Optical fibers 22 were connected to chip 18, aligned to input 14 and output 16 waveguides. Although device 5 is depicted in FIG. 3 as having 5 coupled micro-ring resonators 12, the current invention contemplates any number of micro-ring resonators 12 on device 5. Further, FIG. 3 depicts each micro-ring resonator 12 coupled to a single input waveguide 14. However, alternative embodiments may provide a separate input waveguide 14 for each micro-ring resonator 12.

The gain of coupled resonators 10 can be controlled by adjusting the geometry of the resonator, i.e. the size of micro-ring 12. Alternatively, the gain may be controlled by adjusting the area of micro-ring 12 covered by the receptors. For example, if the receptors only cover half of the ring surface, then the gain to detect the rate of changes is reduced by half. For mass transportation dominated condition, this is still true, as mass transport rate is proportional to the surface area that covered by the receptors. Alternatively, adjustments may be made in receptor density on micro-ring resonator 12 which in turn will alter the binding rate of the analyte to the receptors without changing the mass transportation rate. Altering receptor density on micro-ring resonator 12 will change the gains only when mass transportation is not dominated, i.e. at low density receptor condition, or when using receptors that have medium to low affinity to the analyte.

In a preferred embodiment, the methods of the current invention utilizes a reader system (not shown) including an optical spectrum analyzer, a broadband light source (1.53-1.61 μm) and an optical switch to determine the initial resonance wavelengths of individual micro-rings 12 on device 5. Preferably device 5 uses a fiber optic tail 22 to provide light communication between device 5 and the light source. For each active resonator 10, the reader system monitors shifts in the resonance wavelengths over time as analyte is captured by the receptors. Input and output waveguides 14, 16 of device 5 were connected to the broadband light source and the OSA respectively, via optical fiber tail 22. The optical switch (not shown) facilitated repeated sequential channeling of light to the five resonators 10. The scan rate for the system was approximately 15 seconds per coupled resonator 10.

Preparation of each coupled resonator 10 for quantitative analysis initially requires attachment of the receptor compounds. In this case, antibody and nucleic acid probe attachment to the micro-rings 12 was achieved by amine-epoxysilane coupling chemistry. Each device 5 is initially derivatized with epoxysilane and then functionalized with either antibodies (for whole cell/antigen detection assays) or amine-modified nucleic acid probes (for detection of target nucleic acid hybridization). Reference resonators 100 may be prepared in a similar manner using similar compounds. However, the compounds attached to reference resonators 100 are selected to provide similar characteristics as the compounds applied to active resonators 10 without actively binding the target analyte. Alternatively, reference resonators 100 may be left blank or may carrying a blocking agent such as but not limited to bovine serum albumin (BSA), polyethylene glycol (PEG) and its derivatives, ethanolamine, and Superblock™ blocking buffer available from Pierce Biotechnology Inc. of Rockford, Ill.

Prior to carrying out epoxysilane derivatization, surfaces are first cleaned by soaking in an appropriate solution. One suitable solution is 1% NaOH in 60/40 ethanol/water. The chips are subsequently rinsed with a solution such as ethanol and water. Epoxysilane-derivatization is carried out by treating the cleaned chips with a solution containing 10% GPTS (3-glycidoxylpropyl trimethoxysilane) and 10 mM acetic acid in 95% ethanol or other suitable solution. Typically, this step is carried out for about 30 minutes. Following silanization, each device 5 is rinsed to remove any excess solution. Rinsing is preferably carried out using 95% ethanol. The attached epoxysilane is cured by baking in an oven heated to about 100° C. to about 140° C. The curing step is generally carried out over a period of about 30 minutes to about two hours. Preferably, the curing period lasts about one hour. Following curing, devices 5 should be stored in a dry environment such as a desiccator until used.

Following drying of the silanized devices 5, commercially available receptors such as monoclonal antibodies are attached to the surface of the micro-ring resonators 12. The monoclonal antibodies are typically suspended in a buffered solution having a pH higher than 7. For example a solution of phosphate buffered saline (PBS) mixed with Sodium hydroxide (NaOH) to give a solution with pH 10 is suitable for use in the current invention. A higher pH favors reaction of the amine groups on antibodies with the epoxide surface. In general, the suspension of monoclonal antibodies in buffered solution should have a concentration of about 0.25 µg/µl to about 2 µg/µL. Following preparation of the suspension, from about 0.5 µL to about 1 µL of the resulting solution is applied over each of the micro-rings and allowed to bind overnight at a temperature between about 4° C. to about 8° C. in a humidified chamber. Preferably, the humidity within the chamber is maintained between about 60 and about 100. However, binding can also be carried out at room temperature at a relative humidity of about 50 to 60% and an incubation time of 1 hour. Further, while overnight binding is preferred it is not absolutely necessary.

As noted above, commercially available receptors, i.e. nucleic acid probes, are suitable for use in the current invention. For example, IDT Inc. of Coralville, Iowa sells probes synthesized with a 5' amino modification and a six carbon spacer. The probes are preferably diluted in a 2× Sodium chloride sodium citrate buffer (SSC) to a final concentration of about 25 µM to about 50 µM. Following dilution, the solution is applied on each of the micro-rings and allowed to bind for about 30 minutes to about 2 hours at room temperature. Preferably, 0.5 µL of solution is applied to the microrings and allowed to dry for two hours. Other biosensing compounds may be attached to micro-rings 12 using similar methods.

Following drying, devices 5 are subjected to a blocking and washing cycle sufficient to remove excess unbound antibodies/nucleic acids and prevent any non-specific binding events on the chip surface subsequent to antibody/nucleic acid binding. After antibody attachment the surface was blocked. Materials suitable for the blocking procedure include but are not limited to the use of 1% bovine serum albumin (BSA) for 30 to 45 minutes followed by rinsing using PBS-Tween (0.5%) solution and followed by two rinses in PBS alone. Each rinse procedure was performed for 10 minutes. Following nucleic acid attachment, devices 5 were similarly blocked and rinsed using 2× Sodium chloride-Sodium phosphate-EDTA buffer (SSPE).

The resulting surface blocked epoxysilane derivatized micro-ring resonator chips are suitable for the detection of different biomolecules. The biomolecules detectible by the microresonator chips are determined by the type of receptor attached to the micro-ring following the silanization step.

Figure 5:
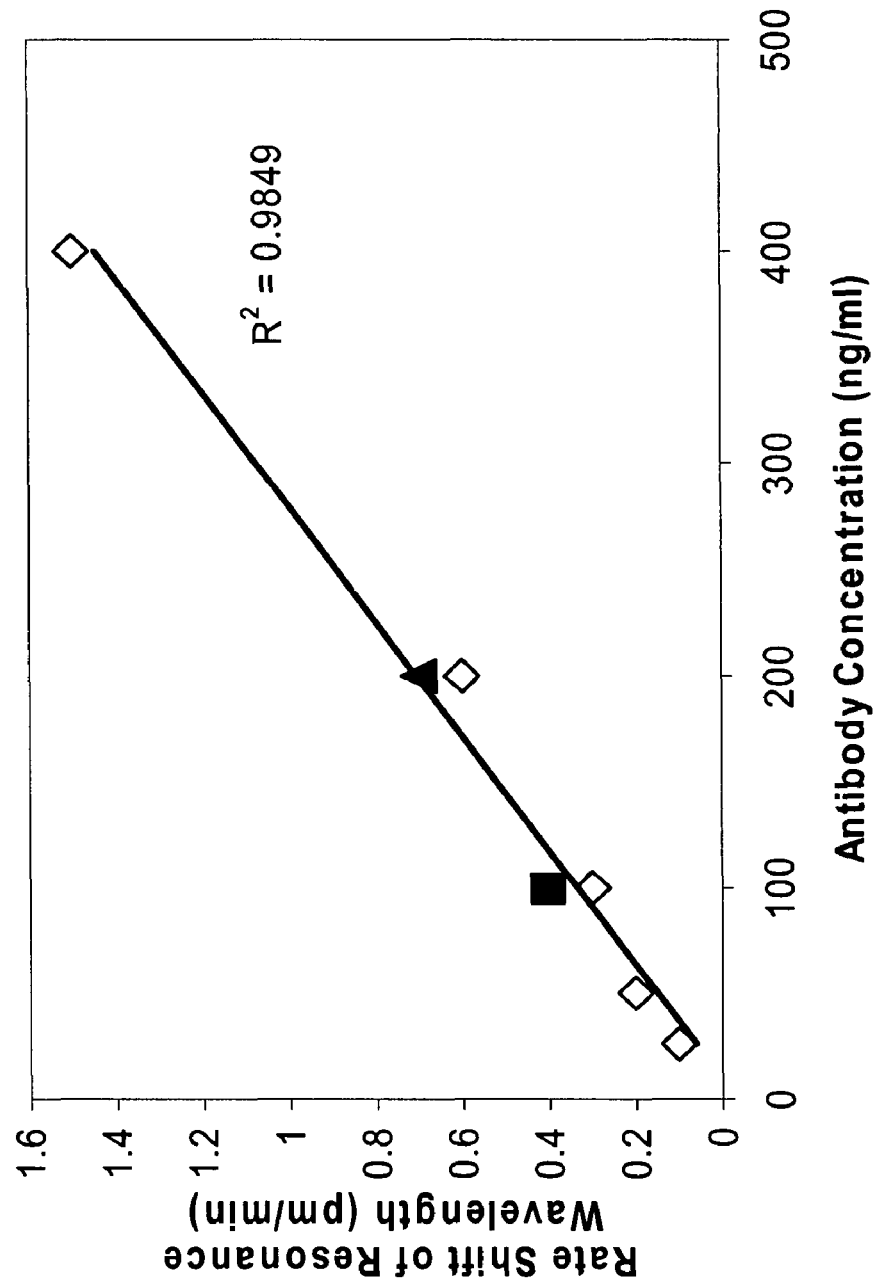
FIG. 5 depicts a calibration curve and demonstrates the ability to determine the concentration of an analyte using the methods of the current invention.

Using the device of FIG. 3 prepared according to the above methods will permit the determination of the concentration of a target analyte by measuring the rate of shift in resonance wavelength experienced by active resonators 10 in comparison to reference resonator 100 when exposed to a solution or suspension carrying the target analyte. As reflected by FIG. 5, the rate of shift in resonance wavelength of active resonators 10 reflects a linear relationship to analyte concentration. As discussed below, FIG. 5 is a standard curve of the shift in resonance wavelength generated from the sequential exposure of the device 5 to known concentrations of IgG. The curve depicts the net rate shift in resonance wavelength averaged from 10 minutes of exposure to different IgG concentrations. It was estimated that under mass transportation limited binding conditions, exposing device 5 for a short period of 10 minutes to relatively low concentration of analyte (IgG) would only allow a very small portion of the analyte to be captured to active resonator 10, thereby leaving the binding rate of IgG to the receptors, in this case surface immobilized monoclonal antibodies, effectively unchanged and remaining higher than the mass transportation rate.

Therefore, when the same device 5, or any other embodiment thereof, is subsequently exposed to IgG "test" samples the standard curve equation can be used to calculate values for the test samples.

Referring again to FIG. 3, the method of the current invention utilizes an array 20 of vertically coupled resonator devices 10 wherein at least one coupled resonator 10 is an active sensing resonator 10 and at least coupled resonator 10 is a control resonator 100. Light injected into the input waveguide 14 weakly couples to micro-ring 12 that supports resonant modes at very specific wavelengths. At these wavelengths, light continuously recirculates in micro-ring 12, giving an effective path length that is much longer than the physical size of the ring and enhancing sensitivity. An evanescent optical field extends outside micro-ring 12 to a range of a few hundred nanometers and is capable of sensing refractive index changes in the environment immediately surrounding micro-ring 12.

The methods of the current invention provide the ability to perform multiple quantitative measurements of relatively low analyte concentrations without the need to regenerate the receptors carried by micro-ring 12. When the rate of mass transport is the rate limiting factor, the binding rate of the analyte to the receptors will be determined by the combination of diffusion rate and the concentration of analyte. Since the diffusion rate is typically constant, the analyte concentration is linearly proportional to the binding rate. Under these conditions, partial saturation of the receptors by bound analytes will not affect the net binding rate.

In the method of the current invention, data from the active resonator 10 and control or reference resonator 100 are collected and analyzed in real time. As a result, analyte exposure time to the receptors is minimized. Typically, analyte exposure to the receptors will last from about 30 seconds to about 60 minutes. Actual exposure time will vary depending on the concentration and the mass transportation rate of the analyte. By limiting total exposure time to that needed to acquire necessary data, multiple quantitative measurements can be performed without saturating the receptors, thus minimizing the need for regeneration. Additionally, continuous referencing of the control resonator 100 to the active resonator 10 substantially eliminates any environmental effects or nonspecific binding on the resulting determination of analyte concentration. In the preferred embodiment, all environmental effects or results from non-specific binding will be eliminated by the present invention.

The binding of an analyte (A) to a surface receptor such as a ligand (L) coating the surface of a sensor resonator can be modeled as a two step process involving (i) analyte transport to the sensing surface, followed by (ii) the reversible ligation reaction, as expressed by:

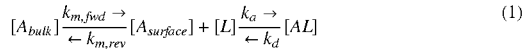

where $[A_{bulk}]$ is analyte concentration in bulk solution, $[A_{surface}]$ is analyte concentration at the sensing surface, [L] is the concentration (effective surface density) of free receptors, i.e. ligands, [AL] is the concentration (effective surface density) of bound receptors, i.e. ligands with attached analyte, $k_{m,fwd}$ is the analyte mass transport coefficient from bulk solution to the surface, $k_{m,rev}$ is the analyte mass transport coefficient from the surface to the bulk solution, $k_a$ is the ligand association rate constant, and $k_d$ is the ligand dissociation rate constant. Generally, the forward and reverse mass transport coefficients are considered to be identical (i.e., $k_{m,fwd}=k_{m,rev}=k_m$).

In general, the receptors are high-affinity ligating surface species, such as a high-affinity Abs, where $k_a$ is significantly higher than $10^6$ $M^{-1}S^{-1}$-$10^9$ $M^{-1}S^{-1}$ typical). In addition, for low analyte concentrations (hundreds of nanograms to picograms/ml), non-steady state conditions exist where $[A_{surface}]$<$[A_{bulk}]$<<[L]. These conditions are classically associated with mass transport as the binding reaction rate-limiting step. Under these conditions, as long as the density of free receptors remains relatively large compared to the activity of surface receptors, the binding rate is proportional to the bulk analyte concentration.

In one aspect, coupled resonator 10 acts as a bound mass transducer which experiences a change in the effective refractive index of the optical modes in the resonator corresponding to the binding of the analyte to the receptors. The transducer response, measured as a rate of change in the model effective refractive index, changes linearly as a function of the total mass of bound analyte. By choosing an interrogation wavelength or band of wavelengths where the analyte does not show significant absorption, there is essentially no change in the resonator Q. Thus, coupled resonator 10 maintains the desired narrow resonance (high Q) as well as a high signal to noise ratio.

The change in resonant wavelength, Δλ, due to a change in RI surrounding the ring, is given by the relationship:

$$\frac{\Delta \lambda}{\lambda} = \alpha \frac{\Delta n}{N_e}$$

where λ is the operating wavelength, $N_e$ is the effective index of the ring mode, Δn is the refractive index change, and α is the fraction of optical power propagating in the region where sensing takes place. A shift in wavelength resulting from bioanalyte detection is a measure of the instrument sensitivity. Relationship (1) shows that the shift in wavelength (Δλ) is directly related to the index change (Δn) resulting from a biochemical reaction, and the amount of optical signal (α) actually propagating in the region where the reaction takes place. While Δn depends on the type of species detected, α depends on the waveguide design.

Assuming coupled resonator 10 is operated under mass transport limiting conditions described above, it can be shown that:

$$d\lambda/dt = C_i [A_{bulk}] \quad (2)$$

where $C_i$ is a conditional constant that varies as a function of the particular experimental conditions under which the measurement is made. The significance of this relationship is that the measured resonator wavelength shift will vary linearly as a function of the bulk solution analyte concentration as long as the premised $[A_{surface}]$<$[A_{bulk}]$<<[L] conditions prevail.

Thus when applied to the current invention, the binding of analyte in the active resonator 10 will produce a change in resonance wavelength while any change produced by contacting reference resonator 100 with the same sample will not be due to binding of the analyte to surface receptors. The net rate of change of the resonance can be determined by observing the rate of change in resonant wavelength from an active resonator 10 and subtracting the rate of change observed in a near identical reference resonator 100. By comparing the two rates of change, a real time measurement of the rate of change in resonance is determined that is directly proportional to the analyte concentration and is not susceptible to interference by nonspecific binding or other environmental effects, such as changes in temperature.

In one embodiment, the invention requires the use of at least one active resonator 10 and a reference resonator 100. In the example shown in FIG. 3, there are four active resonators 10 and one reference resonator 100. Each active resonator 10 is coated with any of a number of different chemical or biological binding agents in such a way as to multiplex the detection of multiple analytes in a single sample using a single integrated optical device 5. As an example, the receptors on active resonator 10 are surface immobilized anti-human IgG antibodies while reference resonator 100 utilizes receptors of IgM mouse monoclonal antibody ligands. Assuming no presence of IgM in the analyte sample of interest, the net rate of change of the resonance from the active resonator 10 coated with IgG, after subtracting the rate of change of reference resonator 100 in real time, will correspond to the current, analyte concentration of IgG in the sample. Alternatively, since the calculation of analyte concentration is based on the rate of change of resonator 10 compared to reference resonator 100, reference resonator 100 may be a bare micro-ring resonator lacking any receptors. In another alternative, reference resonator 100 may be treated with blocking agents such as, but not limited to, bovine serum albumin (BSA), polyethylene glycol (PEG) and its derivatives, ethanolamine, and Superblock™ blocking buffer available from Pierce Biotechnology Inc. of Rockford, Ill.

For the design in FIG. 3, add and drop waveguides 14, 16 are shown as laterally coupled to micro-ring resonators 12. In practice, one or both of add and drop waveguides 14, 16 may reside adjacent and coplanar with micro-ring resonator 12 or they may reside on a second plane or layer underneath micro-ring resonator 12. In this case, the optical signal is vertically coupled to micro-ring resonators 12. In some cases, vertical coupling may be more desirable as the coupling gap itself can be fabricated such that it is not affected by the presence of the analyte sample, and hence the coupling strength between waveguide and resonator is constant during the measurement process.

As depicted, resonators 10 utilize micro-ring resonators 12; however, the geometry of micro-ring resonators 12 may be of a more general form such as but not limited to ellipse or racetrack configurations that support a single transverse spatial optical mode. Thus, for the purposes of this disclosure, micro-ring resonator 12 includes circular, elliptical and other suitable ring type structures capable of generating the necessary evanescent field.

For proper referencing, the active resonator 10 and reference resonator 100 must be nearly identical, and the same optical modes near in wavelength should be chosen for comparison from the set of supported polarizations (TE and TM) of temporal modes. In alternate variations, resonators 10, 100 may be fabricated such that three sides are exposed and coated with the receptors, i.e. the top and two sidewalls (not shown) or alternatively, the resonator core waveguide may be planarized such that only the top surface of the waveguide is coated with the sensing layer and subsequently exposed to analyte samples. The latter approach is a method of creating a resonator device such that a lateral coupling approach may be used to link waveguide and resonator in such a way that the coupling strength or efficiency is not effected by the presence of the analyte sample itself.

The resonator waveguide surfaces may be coated with receptors using a number of approaches. One simple approach is to simply print or drop the sensing medium selected as the receptors locally onto the surface of each micro-ring resonator 12. Alternatively, a global patterning technique such as photolighography may be used to selectively coat only the active micro-ring with the analyte binding agent through a dip or spin coating process.

Analyte samples may be exposed to the integrated optical resonator device 5 shown in FIG. 3 in a number of ways. The entire device 5 may be used in a dipstick-like approach where it is inserted into a well or container holding the analyte of interest. The device 5 may be held in place long enough to acquire an accurate binding rate, and hence analyte concentration, and then removed and rinsed before exposure to a new analyte sample. Alternatively, a flow cell (not shown) could be used to stream an analyte sample over active resonators 10 and reference resonator 100. Once the data is acquired, the analyte stream could be switched off and the device 5 rinsed in-situ before exposure to a second analyte stream. Multiple analyte measurements may be taken up to the point where the receptors begin to approach saturation and the binding rate is limited by the availability of receptor binding sites on the surface rather than the rate of mass transport. At this point, a new device 5 can be used or resonators 10 and reference resonator 100 regenerated to reactivate the receptors.

When using the device of FIG. 3, the relative rate of change in the resonant wavelength of one of the active resonators 10 may be measured by periodically sweeping the wavelength of a narrow-band-tunable light source such as a tunable laser (not shown) coupled to input waveguide 14 across each resonance such that a signal appears on the detector (not shown) when the input wavelength matches the resonance of coupled resonator 10. The rate of change in the temporal separation between the detector signal from one of the active resonators 10 as compared to the reference resonator 100 will correspond to the analyte concentration.

Alternatively, an electronic algorithm may be devised to derive and add a variable time delay to the detector signal corresponding to active resonator 10 such that it matches the output of reference resonator 100 over time. In this case, the rate of change in the variable time delay will correspond to the analyte concentration.

A second example embodiment of the current invention is shown in FIG. 4. In this example, there is a single active resonator 10 and one reference resonator 100. In this configuration a broader band optical source, such as a light-emitting diode (LED) (not shown), may be used for the optical input. It may be necessary to employ an optical splitter and/or and optical bandpass filter (not shown) in addition to input waveguide 14. Active resonator 10 and reference resonator 100 will each drop an optical signal onto drop waveguide 16 corresponding to resonant wavelength of the resonators 10, 100. By combining the outputs onto the same drop waveguide 16 and guiding the two signals to the same detector (not shown), a homodyne detection scheme can be used. If resonators 10, 100 are similar and the drop signals are close enough in wavelength to be at least partially coherent, they will beat on the detector over time at a frequency related to the relative difference in the rates of change of the resonant wavelengths of the two resonators 10, 100. Thus, the beat frequency of the signals will be directly related to the analyte concentration. In this embodiment, one method for determining analyte concentration is to develop a standardized curve as discussed above. Thus, when no analyte is present in a test sample, there will be no detectible beat frequency.

The following example demonstrates the steps and equipment suitable for quantitatively determining the presence of a target analyte. This example demonstrates one embodiment of the current invention. Neither the equipment used nor the example should be considered to limit the scope of the current invention. The method utilizes a reader system consisting of an optical spectrum analyzer (OSA, ANDO-AQ6317B), a broadband light source (1.53-1.61 μm, Thorlabs Inc. —ASE-FL7002) and an optical switch (JDS Uniphase) to determine initial resonance wavelengths of individual micro-rings 12 on device 5. In this example, device 5 uses a fiber optic tail 22 to provide light communication between device 5 and the light source (not shown). The reader system also monitors shifts in the resonance wavelengths over time as analyte is captured by the receptors. Input and output waveguides 14, 16 of device 5 were connected to the broadband light source and the OSA respectively, via optical fiber tail 22. The optical switch (not shown) facilitated repeated sequential channeling of light to the five resonators 10. The scan rate for the system was approximately 15 seconds per coupled resonator 10.

Preparation of each coupled resonator 10, 100 for quantitative analysis initially requires attachment of the receptor compounds. In this case, antibody and nucleic acid probe attachment to the micro-rings 12 was achieved by amine-epoxysilane coupling chemistry. Each device 5 is initially derivatized with epoxysilane and then functionalized with either antibodies (for whole cell/antigen detection assays) or amine-modified nucleic acid probes (for detection of target nucleic acid hybridization).

Prior to carrying out epoxysilane derivatization, surfaces were first cleaned by soaking in a solution containing 1% NaOH in 60/40 ethanol/water for 30 minutes. The chips 18 were then rinsed with copious amounts of ethanol and water. Epoxysilane-derivatization was achieved by treating the cleaned chips 18 with a solution containing 10% GPTS (3-glycidoxylpropyl trimethoxysilane) and 10 mM acetic acid in 95% ethanol for 30 minutes. Following silanization, each device 5 was rinsed thoroughly with 95% ethanol. The coated epoxysilane layer was cured by baking in an oven at 120° C. for one hour. Devices 5 were stored in a desiccator until used for antibody or nucleic acid probe attachment.

Following drying of the silanized devices 5, commercially available monoclonal antibodies were attached to the surface of the micro-ring resonators 12. The monoclonal antibodies are typically suspended in a buffered solution having a pH higher than 7. For example a solution of phosphate buffered saline (PBS) mixed with Sodium hydroxide (NaOH) to give a solution with pH 10 is suitable for use in the current invention. A higher pH favors reaction of the amine groups on antibodies with the epoxide surface. In general, the suspension of monoclonal antibodies in buffered solution should have a concentration of about 0.25 µg/µL to about 2 µg/µL. Following preparation of the suspension, from about 0.5 µL to about 1 µL of the resulting solution is applied over each of the micro-rings and allowed to bind overnight at a temperature between about 4° C. to about 8° C. in a humidified chamber. Preferably, the humidity within the chamber is maintained between about 60 and about 100. However, binding can also be carried out at room temperature at a relative humidity of about 50 to 60% and an incubation time of 1 hour. Further, while overnight binding is preferred it is not absolutely necessary.

As noted above, commercially available nucleic acid probes, i.e. receptors, are suitable for use in the current invention. For example, IDT Inc. of Coralville, Iowa sells probes synthesized with a 5' amino modification and a six carbon spacer. The probes are preferably diluted in a 2× Sodium chloride sodium citrate buffer (SSC) to a final concentration of about 25 µM to about 50 µM. Following dilution, the solution is applied on each of the micro-rings and allowed to bind for about 30 minutes to about 2 hours at room temperature. Preferably, 0.5 µL of solution is applied to the micro-rings and allowed to dry for two hours.

Following drying, devices 5 were subjected to a blocking and washing cycle sufficient to remove excess unbound antibodies/nucleic acids and prevent any non-specific binding events on the chip 18 surface subsequent to antibody/nucleic acid binding. After antibody attachment the surface was blocked. Materials suitable for the blocking procedure include but are not limited to the use of 1% bovine serum albumin (BSA) for 30 to 45 minutes followed by rinsing using PBS-Tween (0.5%) solution and followed by two rinses in PBS alone. Each rinse procedure was performed for 10 minutes. Following nucleic acid attachment, devices 5 were similarly blocked and rinsed using 2× Sodium chloride-Sodium phosphate-EDTA buffer (SSPE).

The resulting surface blocked epoxysilane derivatized micro-ring resonator chips 18 are suitable for the detection of different biomolecules. The biomolecules detectible by the microresonator chips 18 are determined by the type of receptor attached to the micro-ring 12 following the silanization step.

When micro-ring resonator chips 18 are modified with organism-specific monoclonal antibodies targeting antigens expressed by the organism such as lipopolysaccharides (LPS), outer membrane proteins (OMPs) or other unique antigenic entities, the microresonator chip 18 will be capable of detecting bacteria such as E. coli O157:H7. When detection of bacteria is desired, the control micro-rings 100 on the same chip 18 as the active micro-rings 12 are coated with a non specific monoclonal antibody that does not bind to the targeted bacteria. To determine the presence of the target bacteria, the micro-ring resonator chip 18 is typically dipped in 2 mL of PBS to determine the initial resonance wavelengths of the micro-rings using the reader system. Subsequently, the micro-rings are standardized by exposure to different dilutions of E. coli O157:H7 broth. The shift in resonance wave lengths of the test and control rings are monitored overtime and used to establish a curve against which unknown samples may be measured.

Similarly, the micro-ring resonator array 20 may be used to detect and determine the concentration of small proteins in serum. In this embodiment of the current invention, different micro-rings 10 of an micro-ring resonator chip 18 are coated with monoclonal antibodies available from Biodesign International, Saco, Me., USA against S100B. The S100B protein is a 22 kDa brain injury biomarker protein which exists as a dimmer. The control micro-rings are coated with non-specific monoclonal antibodies. Using the reader system, initial baseline resonance wavelengths for each ring is established with the micro-ring resonator chip 18 immersed in 2 mL human serum (Bioreclamation Inc.). A standardization curve is established by adding S100B to the serum and the micro-ring resonator chip 18 was incubated in it for approximately 1 hour. A second monoclonal antibody (reporter MAb) recognizing a different epitope on S100B was subsequently added to the serum at a concentration of 1 µg/mL and the shift in resonance wavelength was monitored overtime.

In another embodiment, the current invention is suitable for detecting nucleic acids associated with viruses. In this method, micro-rings are coated with synthetic DNA oligonucleotide probes modified to have a six carbon spacer and a $NH_2$ group at the 5' end. Two DNA probes (IDT Inc., Table 1), targeting specific sequences in the genomes of Bovine Herpes Virus (BHV) and Bovine Viral Diarrhea Virus (BVDV), were coated on different micro-rings of the same micro-ring resonator chip 18. Using the reader system initial resonance wave lengths of individual micro-rings modified with oligonucleotide probes were determined in 2×SSPE. The chip 18 was then exposed to 500 nM of synthetic target oligonucleotides (IDT Inc., Table 1). Shifts in resonance wavelengths were monitored over time.

In yet another embodiment, the current invention provides for determining the concentration of a target analyte in real time using micro-ring resonators coated with monoclonal antibodies against the target bioanalyte. As discussed above, following application of the receptors and blocking, base-line resonance wavelengths of individual micro-rings are established in a buffer solution using the reader system. The buffer is then spiked sequentially with different concentrations of the target analyte. Preferably, at least 3 concentrations will be used to establish a standardized curve. More preferably, at least 5 concentrations of the analyte will be used to establish the standardized curve. Shifts in resonance wavelength were monitored for about 10 minutes at each concentration and a standard curve was generated based on the net shift at each concentration. The chip 18 was then transferred to fresh buffer solution and exposed to the unknown concentration of the analyte for about 10 minutes while monitoring the shift in resonance wavelength. The resulting shift in resonance wavelength is plotted on the standardized curve and the concentration of the analyte in the unknown is calculated.

In another example, different micro-rings 12 of device 5 as depicted in FIG. 3 were coated with monoclonal antibodies against human IgG and a control monoclonal antibody. Baseline resonance wavelengths of individual micro-rings 12 were established in PBS buffer using the reader system. The buffer was then spiked sequentially with different concentrations of polyclonal IgG, resulting in final concentrations of 25, 50, 100, 200 and 400 ng/mL of PBS buffer. Rate shifts in resonance wavelength were monitored for 10 minutes at each concentration and a standard curve was generated based on the net rate shift at each concentration. The respective results for each standard concentration are represented in FIG. 5 by the diamonds. Device 5 was then transferred to fresh buffer solution and exposed to two "test" concentrations (100 ng/mL and 200 ng/mL) of IgG for 10 minutes each while monitoring the rate shift in resonance wavelength. The results for the 100 ng/mL sample are depicted on FIG. 5 by the solid square and the results for the 200 ng/mL sample are depicted with a solid triangle.

The rate of shift in resonance wavelength of micro-rings 12 showed a linear relationship to analyte concentration under the experimental conditions. FIG. 5 indicates that a standard curve of the shift in resonance wavelength was generated from the sequential exposure of the device 5 to increasing concentrations of IgG. The curve depicts the net rate shift in resonance wavelength averaged from 10 minutes of exposure to different IgG concentrations. It was estimated that under mass transportation limited binding conditions, exposing device 5 for a short period of 10 minutes to relatively low concentration of analyte (IgG) would only allow a very small portion of the analyte to be captured to active resonator 10, thereby leaving the binding rate of IgG to the receptors, in this case surface immobilized monoclonal antibodies, effectively unchanged and remaining higher than the mass transportation rate.

Therefore, in this example the mass transportation rate controls the rate changes of the micro-ring thereby resulting in a linear relationship between the solution concentration of the analyte and time. As a result, measurements of multiple samples can be performed using the same device 5 as depicted in FIG. 3, or any other embodiment thereof, without washing or regeneration of the sensor surface. When the same device 5, or any other embodiment thereof, was subsequently exposed to IgG "test" samples at concentrations of 100 ng/mL and 200 ng/mL in fresh buffer, averaged rate shift of resonance wavelength of 0.4 pm/min and 0.7 pm/min (solid square and solid triangle respectively in FIG. 4) were observed. Using the standard curve equation to calculate values for the test samples produces results of 107.5 and 182.5 ng/mL of IgG, respectively. In the foregoing examples, the detection limit for IgG detection is approximately 10 ng/mL for a ten minute binding period.

Other embodiments of the current invention will be apparent to those skilled in the art from a consideration of this specification and/or practice of the invention disclosed herein. Accordingly, the foregoing specification is considered merely exemplary of the current invention. The true scope of the current invention is defined by the following claims.

We claim:

1. A method for determining the concentration of an analyte comprising:
    providing a first coupled resonator comprising, a micro-ring resonator coupled to an input waveguide and an output waveguide, said output wave guide being optically coupled to a detector;
    providing a second coupled resonator comprising, a micro-ring resonator coupled to an input waveguide and an output waveguide, said output wave guide being optically coupled to a detector;
    preparing a sensing micro-ring resonator by applying receptors suitable for binding the analyte of interest to said micro-ring resonator of said first coupled resonator;
    contacting said micro-ring resonators with a solution or suspension containing said analyte while passing light through said input waveguide;
    comparing the rate of change in resonance wavelength of said sensing micro-ring resonator in said first coupled resonator to the rate of change in resonance wavelength of the micro-ring resonator in the second coupled resonator thereby determining the presence and concentration of said analyte.

2. The method of claim 1, further comprising the step of determining the baseline resonance wavelengths of each micro-ring resonator.

3. The method of claim 1, further comprising the step of applying a blocking agent to the micro-ring resonator of said second coupled resonator.

4. The method of claim 1, wherein said micro-ring resonators are contacted with said solution or suspension containing said analyte for a period of time ranging from about 30 seconds to about 60 minutes.

5. The method of claim 1, wherein said micro-ring resonators are contacted with said solution or suspension containing said analyte for a period of time sufficient to induce an alteration in the effective refractive index of said sensing micro-ring.

6. The method of claim 1, wherein said step of comparing the rates of change in resonance wavelength takes place in real time.

7. The method of claim 1, wherein said step of comparing the rates of change in resonance wavelength comprises subtracting the rate of change of the micro-ring resonator of said second coupled resonator from the rate of change of the sensing micro-ring resonator of said first coupled resonator.

8. The method of claim 1, wherein each coupled resonator is positioned on a single chip.

9. The method of claim 8, wherein said chip is an integrated optical resonator device carrying at least three coupled resonators.

10. The method of claim 1, wherein said receptors are label free receptors selected from the group consisting of: antibodies, antigens, nucleotides, analogs, cytokines, engineered proteins, aptamers, proteins, or organic molecules.

11. The method of claim 1, wherein said micro-ring resonator of said second coupled resonator carries blocking agents inert to said analyte.

12. The method of claim 1, wherein said analyte is selected from the group consisting of: proteins, antibodies, cytokines, nucleotides, biomarkers, viruses, bacteria, cells.

13. The method of claim 1, wherein said light passing through said devices is sufficient to generate an amplified evanescent field in said micro-rings.

14. The method of claim 13, wherein said micro-ring resonators are contacted with said solution or suspension containing said analyte for a period of time sufficient to bind said analyte to said sensing micro-ring thereby inducing an alteration in the effective refractive index of said sensing micro-ring.

15. The method of claim 1, wherein said micro-ring resonators are contacted with said solution or suspension containing said analyte for a period of time sufficient to induce an alteration in the effective refractive index of said sensing micro-ring and wherein said step of comparing the rate of change in resonance wavelength takes place immediately upon detection of an alteration in the effective refractive index.

16. The method of claim 1, wherein the wavelength of said light is selected to preclude significant absorption of said light by the target analyte.

17. The method of claim 1, wherein said light has a wavelength between about 200 nm and about 5000 nm.

18. The method of claim 1, wherein said light is generated by a light-emitting diode coupled with an optical splitter.

19. The method of claim 1, wherein said light is generated by a light-emitting diode coupled with an optical bandpass filter.

20. The method of claim 1, wherein said light is generated by a broadband light source and said detector is an optical spectrum analyzer.

21. The method of claim 2, wherein the base-line resonance wavelengths of each micro-rings 12 is established by contacting said micro-rings with a buffer solution.

22. The method of claim 21, further comprising the step of establishing a standardization curve comprising contacting said micro-rings with a second buffer solution containing a first known quantity of said target analyte while observing the resulting rate of change in resonance wavelength in said micro-rings and contacting said micro-rings with at least one additional buffer solution containing a different concentration of said target analyte while observing the resulting rate of change in resonance wavelength in said micro-rings.

23. The method of claim 21, further comprising the step of using said curve to determine the concentration of said target analyte in a test sample.

24. The method of claim 1, where said analyte is brought in contact with said micro-ring resonators by a flow cell.

25. The method of claim 1, where multiple measurements are performed prior to regenerating the sensor micro-ring resonator surface, when the analyte mass transportation rate from the solution to said sensing resonator is lower than the analyte binding rate to the receptor on said sensing resonator.

26. The method of claim 1, wherein the gain of said coupled resonator is adjusted by altering the area covered by said receptors on said micro-ring resonator of said first coupled resonator.

27. A method for determining the concentration of an analyte comprising:
  providing a coupled resonator comprising, a first micro-ring resonator coupled to an input waveguide and coupled to an output waveguide, said output wave guide being optically coupled to a detector;
  providing a second micro-ring resonator, said second micro-ring resonator being coupled to the same input waveguide and output waveguide as said first micro-ring resonator;
  preparing a sensing micro-ring resonator by applying receptors suitable for binding the analyte of interest to said micro-ring resonator;
  directing light through said input wave guide;
  contacting said coupled resonator with a solution or suspension containing said analyte of interest while passing light through said coupled resonator;
  combining light output from each micro-ring onto said output waveguide and directing said light to a detector;
  determining the relative difference in the rates of change of the resonant wavelengths experienced by each micro-ring resonator thereby determining the presence and concentration of said analyte of interest.

28. The method of claim 27, further comprising the step of determining the wavelength of signals received from said active micro-ring resonator and from said reference micro-ring resonator, using said wavelength to determine the relative difference in the rate of change of resonant wavelengths experienced by each micro-ring resonator.

29. The method of claim 27, further comprising the step of applying blocking agents which will not bind said analyte of interest to said second micro-ring resonator.

30. The method of claim 27, wherein said micro-ring resonators are contacted with said solution or suspension containing said analyte for a period of time ranging from about 30 seconds to about 60 minutes.

31. The method of claim 27, wherein said micro-ring resonators are contacted with said solution or suspension containing said analyte for a period of time sufficient to induce an alteration in the effective refractive index of said sensing micro-ring.

32. The method of claim 27, wherein said step of determining the relative difference in the rates of change of the resonant wavelengths takes place in real time.

33. The method of claim 27, wherein said light has a wavelength between about 200 nm and about 5000 nm.

34. The method of claim 27, further comprising the step of establishing a standardization curve comprising contacting said micro-rings with a buffer solution containing a first known quantity of said target analyte while observing the resulting rate shift in resonance wavelength in said micro-rings and contacting said micro-rings with at least one additional buffer solution containing a different concentration of said target analyte while observing the resulting rate shift in resonance wavelength in said micro-rings.

35. The method of claim 34, further comprising the step of using said curve to determine the concentration of said target analyte in a test sample.

36. The method of claim 27, wherein said analyte is brought in contact with said micro-ring resonators by a flow cell.

37. The method of claim 27, wherein the step of determining the relative difference in the rates of change of the resonant wavelengths is a homodyne detection step.

* * * * *